United States Patent
Cinquin et al.

(10) Patent No.: US 7,611,887 B2
(45) Date of Patent: Nov. 3, 2009

(54) MICRO-MUSCLE IN BIOLOGICAL MEDIUM

(75) Inventors: Philippe Cinquin, La Tronche (FR); Olivier Cinquin, La Tronche (FR); Denis Favier, Grenoble (FR); Laurent Orgeas, Voiron (FR); Matthieu Pecher, Meylan (FR); Sonia Pujol, Portet sur Garonne (FR)

(73) Assignee: Universite Joseph Fourier, Grenoble (FR)

( * ) Notice: Subject to any disclaimer, the term of this patent is extended or adjusted under 35 U.S.C. 154(b) by 728 days.

(21) Appl. No.: 10/484,062

(22) PCT Filed: Jul. 17, 2002

(86) PCT No.: PCT/FR02/02556
§ 371 (c)(1), (2), (4) Date: Aug. 3, 2004

(87) PCT Pub. No.: WO03/007844
PCT Pub. Date: Jan. 30, 2003

(65) Prior Publication Data
US 2004/0248269 A1 Dec. 9, 2004

(30) Foreign Application Priority Data
Jul. 17, 2001 (FR) .................. 01 09526

(51) Int. Cl.
*G01N 33/00* (2006.01)
*C12M 1/36* (2006.01)
*C12M 3/00* (2006.01)
*A61F 2/06* (2006.01)

(52) U.S. Cl. .............. 435/286.1; 435/7.93; 435/286.5; 623/1.1; 623/1.11; 623/1.12; 623/1.13; 623/1.14; 623/1.15; 623/1.16; 623/1.17; 623/1.18; 623/1.19; 623/1.2; 623/1.21; 623/1.22; 623/1.45

(58) Field of Classification Search ......... 623/1.1–1.22, 623/1.45; 435/7.93, 286.1, 286.5
See application file for complete search history.

(56) References Cited

U.S. PATENT DOCUMENTS 3,952,741 A * 4/1976 Baker ..................... 424/405
3,995,631 A * 12/1976 Higuchi et al. ........... 604/892.1
4,157,085 A 6/1979 Austad (Continued)

FOREIGN PATENT DOCUMENTS

WO    WO 00/27814    5/2000

(Continued)

OTHER PUBLICATIONS

Micromuscle Ab: "News and Products" Internet, en ligne! XP002197173 Extrait de l'Internet :URL:http://www.micromuscle.com/html/news.html extrait le Oct. 31, 2002 le document en entier.

*Primary Examiner*—Bao-Thuy L Nguyen
*Assistant Examiner*—Jacqueline Diramio
(74) *Attorney, Agent, or Firm*—Lando & Anastassi, LLP.

(57) ABSTRACT

The invention concerns a micro-muscle designed to be immersed in a biological liquid, comprising a deformable chamber whereof one portion at least consists of a semipermeable membrane, said chamber containing a solution capable of osmotic activity. The solution is preferably activated by a product to be injected into the biological liquid.

8 Claims, 4 Drawing Sheets

U.S. PATENT DOCUMENTS 4,183,102 A * 1/1980 Guiset ..................... 623/1.25
4,207,890 A * 6/1980 Mamajek et al. ............ 424/473
4,925,446 A * 5/1990 Garay et al. ........... 604/103.02
5,005,591 A * 4/1991 Austad ..................... 128/899
5,100,933 A 3/1992 Tanaka et al.
5,496,368 A * 3/1996 Wiese ......................... 623/8
5,499,994 A * 3/1996 Tihon et al. ................ 606/192
6,776,999 B1 * 8/2004 Krumme .................... 424/451

FOREIGN PATENT DOCUMENTS

WO     WO 00/78222 A1    12/2000

* cited by examiner

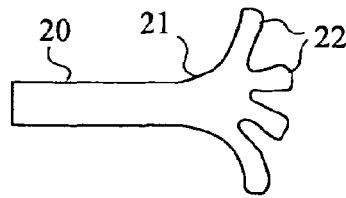
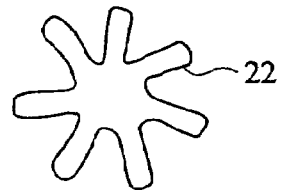
Fig 10A　　　　　　　Fig 10B
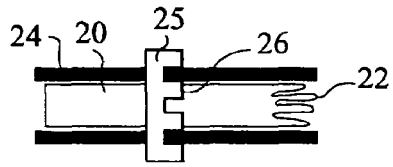
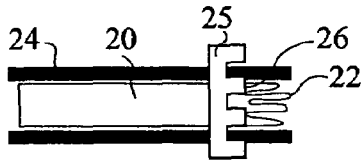
Fig 11A　　　　　　　Fig 11B
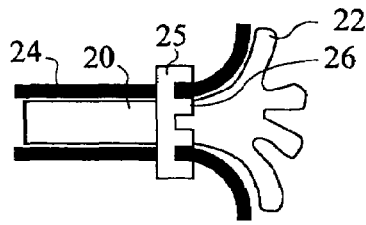
Fig 11C
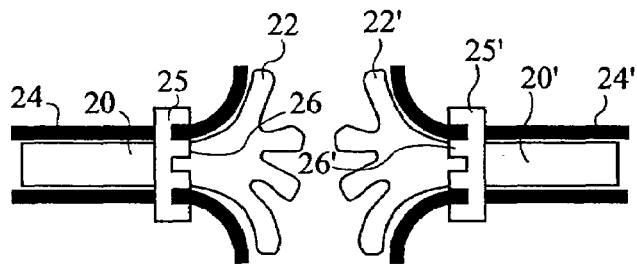
Fig 12A
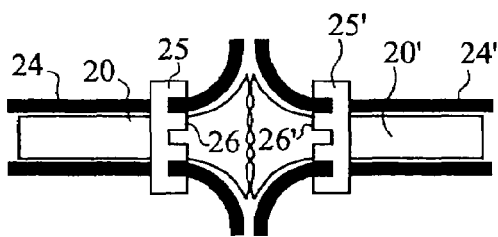
Fig 12B
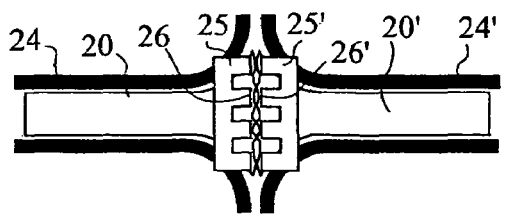
Fig 12C

MICRO-MUSCLE IN BIOLOGICAL MEDIUM

The present invention relates to devices that can be used as a temporary or definitive actuator or endoprosthesis within a biological medium such as the human body or an animal body.

The present invention especially finds applications as a ring-shaped endoprosthesis or stent that can be used to compensate an arterial stenosis, or as an intervention means to aid the sewing, clipping, or jointing of blood vessels, to obturate a vessel, to fill up a cavity, or to have an element such as a needle act against an internal wall of a biological medium such as a human or animal body.

Inflatable balloons or shape-memory devices, which all exhibit disadvantages, as will be discussed hereafter, are conventionally used to perform such operations.

More specifically, the present invention provides a micromuscle intended to be immersed in a biological medium, comprising a deformable chamber having at least a portion formed of a semipermeable membrane, this chamber containing a solute likely to be osmotically active, the chamber being designed to have, after inflating by osmotic effect, a predetermined shape.

According to an embodiment of the present invention, the solute is activable by a product injectable into the biological medium.

According to an embodiment of the present invention, the solute is bound to an attachment matrix from which it can detach in consequence of a competition with another body.

According to an embodiment of the present invention, the solute is bound to HABA molecules, themselves bound to attachment matrixes by proteins, such as avidin or streptavidin derivatives, this bond being breakable by competition with biotin or the like.

According to an embodiment of the present invention, the solute is bound to avidin molecules, themselves bound to attachment matrixes by HABA particles, this bond being breakable by competition with biotin or the like.

According to an embodiment of the present invention, the molecules of biotin or the like are likely to be monomers or dimers.

According to an embodiment of the present invention, the solute is encapsulated in at least one envelope to be destroyed by a physical or chemical reaction.

According to an embodiment of the present invention, the solute is formed of macromolecules likely to be broken by physical or chemical action.

According to an embodiment of the present invention, said chamber comprises a first portion made of a resilient material of desired shape, communicating with a second portion forming a semipermeable membrane, for example in the form of fibers.

According to an embodiment of the present invention, said chamber or its first resilient portion is torus-shaped.

According to an embodiment of the present invention, said chamber or its first resilient portion is likely to deform longitudinally.

According to an embodiment of the present invention, said chamber or its first resilient portion is a substantially spherical deformable volume.

According to an embodiment of the present invention, said chamber under its first resilient portion is formed of two half-cylinders sliding one inside of the other.

According to an embodiment of the present invention, said chamber or its first resilient portion is surrounded with sheath or net determining its definitive shape.

According to an embodiment of the present invention, the solute is albumin.

According to an embodiment of the present invention, the semipermeable membrane of the micromuscle is in communication with a second chamber formed of a flexible material and containing a reserve of a liquid likely to form a solution with a solute contained in the first chamber.

According to an embodiment of the present invention, the second chamber contains a solute likely to be released by physical or chemical action.

The present invention also provides a device for inserting needles into a wall of a vessel filled with a biological liquid, comprising a guide, needles to which a wire is firmly attached on a first side of the guide, the needles being likely to be laid flat on the guide, first osmotic micromuscles on the first side of the guide, likely to erect the needles, and at least one second osmotic micromuscle arranged on the opposite side of the guide.

The present invention also provides a device for aiding the clipping comprising a micromuscle insertable at the end of a cut up vessel, comprising a cylindrical body, digitized ends.

The present invention also provides a use of the above-mentioned micromuscle, in which the micromuscle is torus-shaped and is intended to be used as a joint at the connection between two ducts, such as a cylindrical endoprosthesis and a blood vessel.

The present invention also provides a use of the above-mentioned micromuscle, in which the micromuscle is torus-shaped, expandable outwards and is intended to obturate a duct or a cylindrical endoprosthesis arranged in this duct.

The present invention also provides a use of the above-mentioned micromuscle, in which the micromuscle is in the form of a bag or cylinder expandable outwards and is intended to obturate a duct.

BRIEF DESCRIPTION OF THE DRAWINGS

The foregoing objects, features, and advantages of the present invention will be discussed in detail in the following non-limiting description of specific embodiments in connection with the accompanying drawings, among which:

FIGS. 10 to 12 illustrate an example of application of the present invention to a clipping operation.

The present invention provides a micromuscle or micro-engine that can operate in a biological medium. This micromuscle comprises a chamber formed at least partially of a semipermeable membrane enabling transfer of a solution by osmosis and containing a solute likely to dissolve in a fluid contained in the biological medium. The solute will be selected to be unable to cross said semipermeable membrane. Its presence induces an osmotic pressure likely to cause liquid transfers towards the chamber; the solute will thus be said to be "osmotically active".

The chamber may be placed in compressed or folded form in a selected area of a biological medium, for example, at a given level of an artery, via a catheter or an endoscope. Once the micromuscle has been arranged, molecules from the solution in which it is placed tend to cross the semipermeable membrane and the micromuscle takes a desired shape under the effect of the penetration of a biological liquid, for example, water, into the chamber.

Examples of micromuscle shapes and structures are given in FIGS. 1 to 6.

Figure 1A:
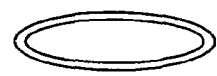
FIGS. 1A to 1C illustrate a first embodiment of a micromuscle according to the present invention.
Figure 1B:
Figure 1C:

FIG. 1A is a perspective view of a torus-shaped micromuscle in expansion. At rest, this micromuscle has either a flattened and possibly folded shape such as shown in FIG. 1B or a compressed or reduced shape as shown in FIG. 1C.

Figure 2A:
FIGS. 2A to 2C illustrate a second embodiment of a micromuscle according to the present invention.
Figure 2B:
Figure 2C:

FIG. 2A is a side view of a micromuscle of cylindrical shape in expansion. At rest, this micromuscle has either a flattened or possibly folded shape such as shown in FIG. 2B or a cylindrical shape of compressed or reduced volume as shown in FIG. 2C.

The chamber such as illustrated for example in FIGS. 1A and 2A may be formed of a semipermeable membrane, possibly formed of a thin semipermeable layer deposited on a porous or perforated support material. This membrane may be resilient or not. For example, to expand from the shape shown in FIG. 1B or 2B to the shape shown in FIG. 1A or 2A, the chamber material needs not be resilient. However, in the case of FIGS. 1C and 2C, the chamber material is a resilient material that expands as adapted.

Various means may be provided to control the final shape and/or the chamber expansion. For example, the chamber will be provided with fibers or surrounded with a net to control its final shape after expansion (flowing of the liquid of the biological medium towards the inside of the chamber).

Figure 3A:
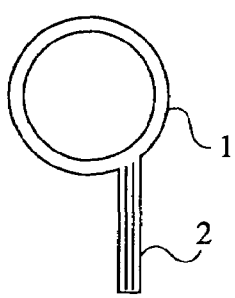
FIGS. 3A to 3C illustrate alternatives of a third embodiment of a micromuscle according to the present invention.

As illustrated in FIG. 3A, the chamber may be formed, on a portion of its surface, of a semipermeable non-expandable membrane, little or not deformable, the rest of its surface being made of a deformable and possibly resilient material connected to the semipermeable membrane. A chamber 1, for example, torus-shaped, made of a resilient material, may be used, the internal volume of which communicates with the internal volume of fibers 2 such as the fibers currently used in hemodialysis operations. The liquid penetrating into fibers 2 will fill up chamber 1 and expand it under the effect of the osmotic pressure. This composite embodiment comprising a first portion formed of an elastic membrane, for example, made of the product sold under trade name Silastic, and a second portion formed of a semipermeable membrane, possibly in the form of fibers, preferably flexible, can adapt to most of the embodiments of the present invention as should be noted by those skilled in the art.

The micromuscle may also be formed of closed fibers with semipermeable walls, initially in a folded state, which tend to straighten and stiffen under the effect of the osmotic pressure.

Figure 3B:
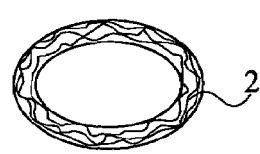

In FIG. 3B, fibers 2 are arranged within a deformable torus-shaped chamber.

Figure 3C:
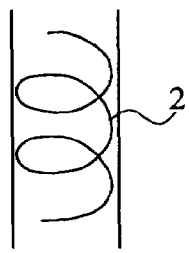

In FIG. 3C, fibers 2 are directly arranged within a cylindrical element to which an expansion force is desired to be applied, for example, a blood vessel. In both cases, the fibers, initially containing molecules enable of crossing the membrane at a concentration greater than the concentration of the biological fluid in molecules themselves unable to cross the membrane, will tend to inflate and straighten, and thus to centrifugally urge the surface surrounding it, once placed in a biological fluid. For the fibers to take, once stiffened, the helicoidal shape illustrated in FIG. 3C, they may be attached in places, possibly slidably, before inflating, to a flexible sheath not shown or to the vessel walls.

In a first version, an assembly of parallel osmotic fibers is sewn to the fabric that forms the wall. The path of any one of these fibers has a spiral shape. When the pressure increases within the fiber, the latter will tend to maximize its volume, and will thus tend to decrease its radius of curvature. Both ends of the osmotic fiber are strongly secured to a specific point of the wall. However, the sewing of the osmotic fiber to the wall is sufficiently loose for the fiber to be able to slide with respect to the wall. The internal diameter of the helix may thus increase, and the wall will tend to expand. The shape taken by the assembly will result from the balance of the centripetal forces exerted by the osmotic fibers and from the resistance against the expansion exerted by the wall.

Various alterations of this version may be envisaged. For example, inextensible wires parallel to the generators of the cylinder formed by the wall may be attached in various fashions (sewing, gluing . . . ) thereto. The attachment is performed to create regular spacings between the inextensible wires and the wall, through which the fibers may pass. These inextensible wires may possibly be semi-rigid rods.

In a second version, the osmotic fibers are directly integrated into the fabric, to the frame of which they take part. An assembly of fibers, for example, made of Dacron, is arranged to form a series of parallel wires. The osmotic fibers are then crossed with this series of parallel wires. Various pattern shapes may be created by the crossing of Dacron fibers and osmotic fibers (for example, the osmotic fibers may have a helicoidal shape, an arrowhead shape . . . ). In an alternative, the fabric is only formed of osmotic fibers.

It should be noted that such a device may find applications outside of the field of vascular endoprothesis design. Indeed, a bag formed of such a fabric can behave as a pump, the motions of which are conditioned by the relative concentration of the liquid medium inside of the bag and of the internal medium of the fibers in osmotically active substances.

Figure 4A:
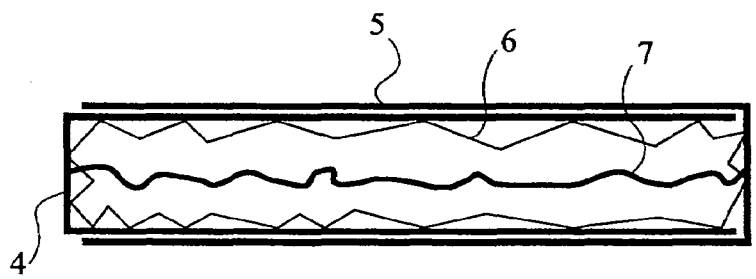
FIGS. 4A and 4B show a fourth embodiment of a micromuscle according to the present invention.
Figure 4B:
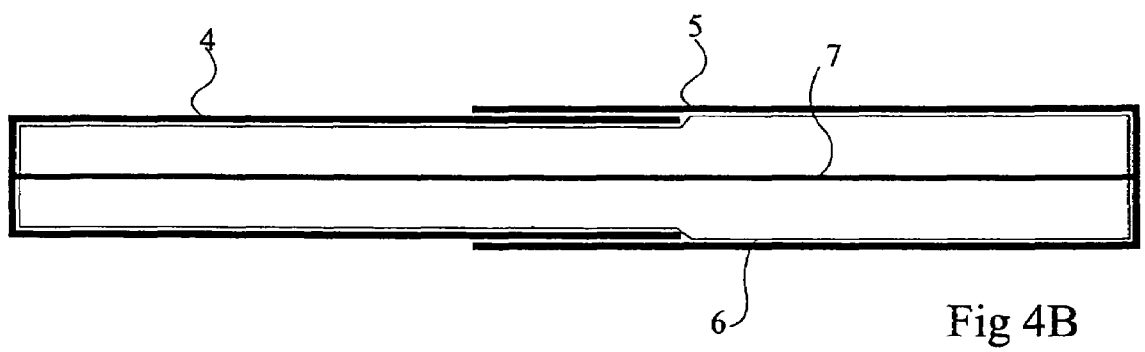

FIGS. 4A and 4B show a fourth embodiment of the present invention, respectively in a state where the micromuscle is contracted, such as it is when put into place, and in a state where it is expanded, after its putting into place and the setting of the osmotic pressure within the chamber. Two half-cylinders 4 and 5 slide one inside of the other. Each of half-cylinders 4 and 5 is closed at its end opposite to the other half-cylinder. Within internal half-cylinder 4 are arranged one or several chambers with a semipermeable wall 6 within which are molecules unable to cross the membrane, not shown. The opposite ends of the two half-cylinders are connected by a wire 7 to limit their extension. As an example, the system in the folded state may have a diameter on the order of 100 µm and a length on the order of from 1 to 3 mm, this length being substantially twice in the unfolded state. The device of FIGS. 4A and 4B may be called a microengine, an active element such as a needle being linkable to one of its ends.

Figure 5A:
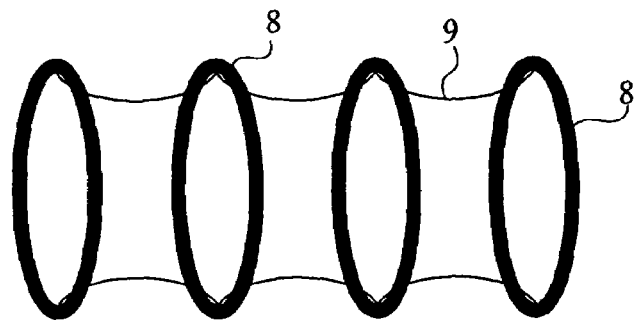
FIG. 5A shows a fifth embodiment of a micromuscle according to the present invention.

FIG. 5A shows another embodiment of the present invention in which several torus-shaped osmotic micromuscles 8 according to the present invention are connected to one another by a net or flexible wires 9, for example, made of Dacron. The toruses may be distant from one another, as shown, or adjacent.

Figure 5B:
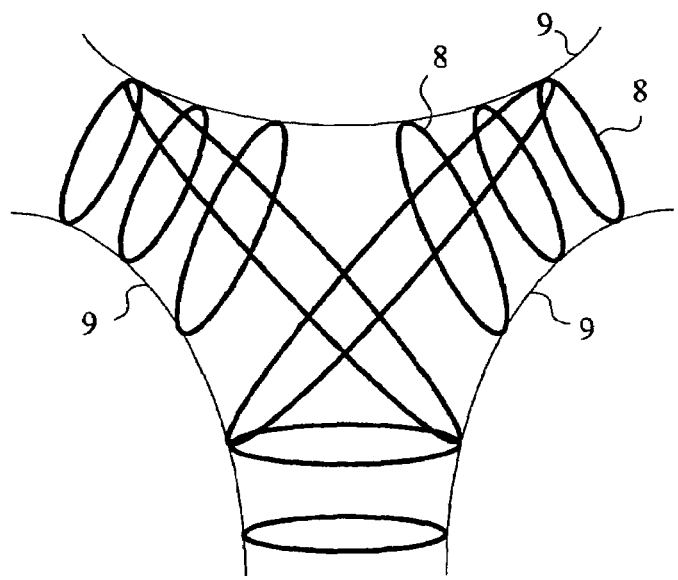
FIG. 5B shows a sixth embodiment of a micromuscle according to the present invention.

FIG. 5B shows another example of a composite micromuscle, the elementary torus-shaped micromuscles being designated with reference numeral 8 and the connection wires or nets with reference numeral 9.

It should be noted by those skilled in the art that the micromuscle according to the present invention is likely to have many other embodiments, and especially many other shapes. It may for example be a bag likely to expand and to take the shape of internal walls of a cavity in which it is placed, for example, to fill a cavity such as an aneurism of a brain vessel or other.

Various solutes, not harmful for the organism in case of a leak, may be used. A known solute is for example albumin, which is not let through by the hemodialysis membrane.

Figure 6A:
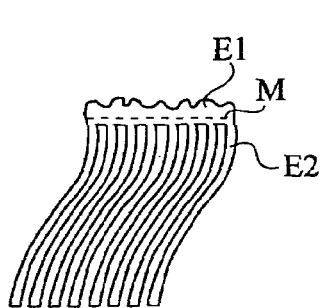
FIGS. 6A and 6B show a seventh embodiment of the present invention.
Figure 6B:
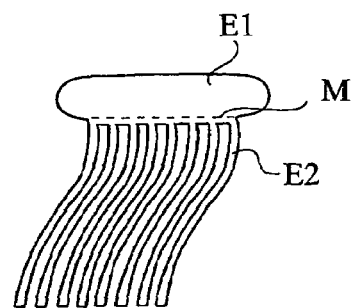

FIGS. 6A and 6B illustrate a seventh embodiment of the present invention, usable in particular when the micromuscle according to the present invention must be inserted into a possibly humid, but non-liquid biological medium. In this case, it may no longer be possible to "pump" the water from the organism. A device comprising two chambers or compartments E1 and E2 communicating through an osmotic membrane M is then provided. In an initial state, compartment E2 contains a fluid and compartment E1 contains a solute likely to dissolve into the fluid of compartment E2. Thus, as illustrated in FIG. 6B, compartment E1 will tend to "inflate" by penetration through membrane M of the fluid contained in compartment E2, the solute contained into compartment E1 dissolving in this fluid. Each of these compartments has a deformable, tight, and biocompatible external envelope. In the example of embodiment illustrated in FIGS. 6A and 6B, chamber E2 has, firmly attached to it, a large number of tight fibers similar to hair or tentacles incapable of obturating a duct or of exerting a force on its walls. However, compartment E1 will have not effect on the walls of a duct in which it is arranged in the "deflated" state illustrated in FIG. 6A, but it will have an obturating or pressure effect in the "inflated" state shown in FIG. 6B. Compartment E1 may have any desired shape, for example, the shape of an inflatable bag illustrated in the drawings or a torus, cylindrical or other shape.

For an insertion into the human body, for example, into a duct or vessel which is desired to be obturated or on the walls of which an action is desired to be exerted, the micromuscles of FIGS. 6A and 6B will first be placed into a catheter in compressed form, that is, compartment E1 will have a reduced volume, the fluid that it contains being pushed out by the pressure towards compartment E2. As soon as the device is put into place, compartment E1 is free to expand and the fluid contained in compartment E2 fills in this compartment which then exerts a desired action in the medium in which it is placed.

Various alterations of this embodiment may be provided. For example, as will be described hereafter, compartment E1 may comprise molecules trapped in a protective envelope or likely to chemically react with other molecules to be activated only when desired. Similarly, compartment E2 may contain non-free solute molecules likely to be released only as a consequence of a physical or chemical action. In this second case, it is possible to "deflate" compartment E1 after insertion and inflating.

Control of the Expansion of an Osmotic Micromuscle

According to an aspect of the present invention, a method for controlling the expansion of a micromuscle according to the present invention is provided. This control may be chemical or physical.

Chemical Control

According to an embodiment of this aspect of the present invention, the micromuscle may contain a solute A likely to react with a body B and to form therewith a solute C, the number of formed molecules of solute C being larger than the number of molecules of solute A consumed upon reaction between A and B. Body B is capable of crossing the semipermeable membrane and solutes A and C are incapable thereof. Body B is then injected into the biological medium, for example, by means of an injection needle. It should be understood that, by performing successive injections, successive "inflatings" of the micromuscle can be performed. Thus, if for example an artery is desired to be expanded, a light expansion may be performed, and subsequently increased. The interval between two injections may be long and will be chosen according to the organism's reactions to the micromuscle.

An implementation of this embodiment is based on the concept of "competition" between chemical bodies. The principle is that a body A can combine, for example, in non-covalent fashion, with two bodies B and C. If A and C are put together in a solvent, a complex A-C will thus form. If, now, B is introduced into the solution, and if B has a greater "affinity" for A than C's for A, B will "move" C: the C molecules will be released, and a complex A-B will form.

This competition principle may be used to increase the osmotic force, for example as follows. Derivatives of specific proteins, such as avidin or streptavidin, covalently bonded to "attachment matrixes" (any solid body used as a support) are used. These proteins play the function of body A for which a competition will occur between body B and body C. Proteins A have the specificity of being able to bind in non-covalent fashion with a molecule of small molecular weight, HABA (4-hydroxyazobenzene-2-carboxylic acid). Body C will be obtained by "grafting" the HABA on a molecule having a sufficient molecular weight not to cross the semipermeable membrane. At the time of its introduction into the organism, the chamber thus contains an attachment matrix, to which is bound in non-covalent fashion, via proteins A, body C. C being attached to the matrix is thus not in solution and has no osmotic effect. A "biotin" derivative, which plays the role of body B, is then introduced into the organism. Biotin is a vitamin with a low molecular weight, naturally present in the organism. Biotin has the specificity of having a very strong affinity for avidin and for streptavidin, much stronger than HABA's affinity for these proteins. Thus, molecules of body C detach from the attachment matrix and form a solute that tends to increase the solution pressure within the chamber.

A, as well as B, will be chosen to obtain a selective affinity of B for A: these molecules will have a very strong reciprocal affinity, while natural biotin will have a lesser affinity for A. The low molecular weight of B will enable it to easily cross the semipermeable membrane. The affinity of B for A will make it compete with C to set on A, thus releasing from the matrix the HABA, and thus, body C, which will then be able to exert its osmotic effect.

It should be noted that it is possible to attach to the matrix, instead of a derivative of avidin or streptavidin, a derivative of HABA, provided to take as C the result of a fusion of a "large" molecule with a derivative of avidin or streptavidin. As in the preceding case, the injection of a biotin analog will "release" C, by competition with HABA.

This alternative, in which C comprises an avidin or streptavidin derivative, has the advantage of enabling partial reversibility of the desired osmotic effect. It is indeed known to generate molecules comprising not a single site having an effect analogous to that of biotin, but two such sites. Call B' such a molecule (which will be called the "dimer" biotin analog form, as opposed to the previously-used "monomer" biotin analog form, which has a single attachment site for an avidin or streptavidin derivative). After C has been released from the matrix (by injection of a monomer biotin analog form), if a dimer biotin analog form is injected, the dimer form will compete with the monomer form. If the dimer form concentration is sufficient, it will move the monomer form from the avidin or streptavidin derivative sites of C. This will translate as the forming of C-B'-C complexes, thus reducing the number of molecules in solution, and thus the osmotic effect. The process may be repeated, by injecting again in a sufficient quantity the biotin analog monomer form. In this case, indeed, the competition will become favorable to the forming of C-B complexes, which increases back the number of molecules in solution.

Although the method has been described to control the osmotic effect of a micromuscle, it also applies to the controlled release of active principles, thus providing an alternative to "implantable syringe" type devices. Such devices exist, and are formed of "tanks" containing the product. Said product is ejected from the tanks under the effect of a physical power source (gas under pressure, osmotic pressure, breakage of the tank wall under the effect of ultrasounds . . . ). The previously-described competition principle has in its application to such devices the advantage of enabling accurate control of the time when the active principle is released (which is an advantage with respect to gas or osmotic effect syringes), and of not requiring use of any device capable of generating and of directing the external power source (which is an advantage with respect to methods using, for example, ultrasounds). It is enough, to achieve this specific object, for body C which will be released to be the active principle of which the release is desired to be controlled, and to be able to cross the chamber in which it is. As soon as the adequate competitor B is introduced into the organism (for example, sublingually, by ingestion or by injection), it will release body C, thus enabling it to diffuse into the organism and to express its medical effect.

It should be noted that, in this alternative of the present invention, the use of a matrix is no longer indispensable, since it is no longer aimed at controlling the osmotic effect. In this case, call C the result of the combination between the active principle and HABA, and call A the result of the fusion between an avidin derivative and a "large" molecule. A and C, put together in the same solution, form an A-C complex. The device inserted into the organism comprises a chamber limited by a membrane impermeable to A-C, but permeable to C, as well as to biotin derivative B. The introduction of B into the organism will move C, which can thus diffuse into the organism.

It should further be noted that the chamber used is not necessarily artificial. There indeed exist in the organism regions into which only certain very specific molecule sorts can penetrate. The natural frontiers of these regions can thus play the function of the previously-used semipermeable membrane. The cephalo-rachidian liquid is an example of such a region, which has the advantage of being easily accessible (for example, by lumbar puncture). Such a region can thus be used as a "tank" and an active principle C such as that discussed in the preceding paragraph can be introduced thereinto, for example, by puncture. Couple (C, B) will in this case be chosen so that B is likely to reach the region of interest. It should be noted that, in the specific case of the cerebrospinal liquid, the release of C will be performed mainly into the areas of cerebrospinal liquid resorption, which are located in the brain. This is particularly advantageous if the preferential activity of C expresses in the brain (L-DOPA, for example, which is a precursor of dopamin, used in the treatment of Parkinson's disease).

It should also be noted that an alternative of the exploitation of the competition properties provided by biotin derivatives may be implemented. Consider a protein having a large internal cavity likely to be used as a tank (such is for example the case for certain "chaperon" proteins such as GroEL, or ferritin). It is possible to configure this protein so that HABA molecules are located at the level of its "aperture" and so that the attachment of avidin or streptavidin proteins is likely to close the cavity. Such a mechanism enables "encapsulating" a large amount of active principle molecules. The introduction of biotin into the organism moves part of the avidin "plugs", thus releasing part of the encapsulated molecules. This system requires for the "tank-protein" and "plug-protein" complexes to be in a medium ensuring their stability and a protection of the immune system, and for this medium to be sensitive to variations of the biotin ratio in the blood. Such conditions can be imposed in an artificial chamber isolated from the organism by an adequate membrane, or obtained in a natural chamber like the cerebrospinal liquid.

It should finally be noted that the provided examples are based on the specific case of the competition between biotin derivatives and avidin or streptavidin derivatives, but that the same results can be obtained with other systems of competition between molecules.

Physical Control

According to an embodiment of this aspect of the present invention, the control can be performed physically, for example by placing part at least of the solute in one or several microcapsules so that it has initially no or little activity. The microcapsules can then be broken, possibly selectively, by means of an external power source, for example, ultrasounds, a magnetic field, or a laser. A body likely to dissolve the microcapsules may also be injected.

It should be noted that physical power may be directly used to "break" molecules into smaller molecules, which has an effect upon the osmotic properties of the solution thus performed. Macromolecules such as DNA may be broken by the application of ultrasounds (this technique is commonly used in molecular biology). The longer the ultrasounds are applied, the more the average fragment size decreases. In an alternative of the present invention, large-size DNA fragments (obtained for example by any protocol of purification of the bacterial DNA, or by "polymerase chain reaction" from the genetic material of the individual to be treated) are placed inside of a semipermeable membrane chosen not to let through such large-size fragments. After the application of ultrasounds, the number of fragments and, accordingly, the osmotic force, increase. The membrane may be chosen to let through DNA fragments of sufficiently small size. In this case, a sufficiently prolonged application of ultrasounds enables releasing part of the DNA from within the membrane, and thus decreasing the osmotic force. It should however be noted that in this alternative, the osmotic force cannot be increased back afterwards.

APPLICATION EXAMPLES

Various examples of applications of an osmotically-inflatable micromuscle according to the present invention will now be described.

1. Vascular Endoprostheses

Methods are known for treating an aneurism, that is, a loss of the parallelism of the edges of a vessel, which translates as an expansion of a vascular segment, consisting of inserting into the vessel, at the expansion level, a cylinder, for example made of a shape-memory material, which is arranged to obturate the communication between the vessel and the aneurism. However, the vessel appears in practice to expand along time and the blood flowing through the vessel can again communicate with the aneurism.

To solve this problem, the present invention provides using, instead of the shape-memory cylinder, a cylinder formed from an osmotic micromuscle according to the present invention. According to an alternative of the present invention, it is provided to use a conventional vascular endoprosthesis formed of a shape-memory material, and to arrange at both ends of this prosthesis a torus-shaped osmotic micromuscle which will behave as a seal of variable and controllable diameter. Indeed, as indicated previously, it may be provided to progressively inflate this torus-shaped micromuscle, at regular intervals, to take into account deformations of the vessel.

2. Progressive Vascular Expansion

Known vessel expansion vascular methods are based on the use of "stents" or ring-shaped springs which are inserted inside of a blood vessel at a location where said vessel is stenosed. Such stents conventionally use memory-shape alloys and face the problem of "restenosis", that is, after having being increased by the expansion gesture, the vessel diameter secondarily decreases, thus depriving the patient of the benefit of the present invention.

The applicant considers that this restenosis is for the most part due to the aggressive character of the expansion. Indeed, with conventional methods, this expansion is performed very rapidly, in certain cases within a few seconds for shape-memory stents and within a few minutes for mechanically-inflated stents. The vessel diameter can be increased by a factor on the order of 2 or more. This results in an inflammatory reaction which will exert on the stent a constrictive effort sufficient to deform it.

The use of a torus-shaped micromuscle according to the present invention enables solving this problem, given that it can be adjusted to very progressively "inflate", for example, within several days. On the other hand, as indicated previously, successive methods for activating the micromuscle according to the present invention may be provided and, at regular intervals, for example, one week, one month or more, the micromuscle may be "reinflated" to perform a very progressive expansion of the vessel to be expanded.

A micromuscle according to the present invention may appear under a particularly small volume in the non-contracted state and can thus easily be inserted by conventional means such as catheters or endoscopes at any desired location.

3. Vessel Suture 3.1. End-to-Side Anastomosis

Coronary artery bypass usually uses a derivation of an artery (for example, the internal mammary artery), which is mobilized and anastomosed just downstream of the stenosed area (end-to-side anastomosis). The diameters of the thinnest coronaries on which such gestures are performed are on the order of from 1.5 mm to 2 mm. The present invention provides a device enabling sewing while respecting the pressure in the vessel (here, the coronary), to ease its handling.

3.1.1. Preparation of the Mammary

The mammary artery may be "equipped" with various mechanisms intended to ease its anastomosis with the coronary. It is indeed possible to introduce a catheter into the free end of the mammary, and to inflate a small balloon around this catheter, which will enable attaching to this end the mechanisms adapted to those which will subsequently equip the coronary (at the possible cost of the subsequent sacrifice of the few vessel millimeters located downstream of the end balloon).

3.1.2. Forming of a "Buttonhole" on the Coronary

A catheter having dimensions smaller than one millimeter is introduced into the coronary, at the level desired for the anastomosis. This introduction can be performed through the femoral.

The catheter comprises a guide. This guide may be immobilized at two points located upstream and downstream of the area to be anastomosed (by means of two clips seizing the coronary).

Figure 7A:
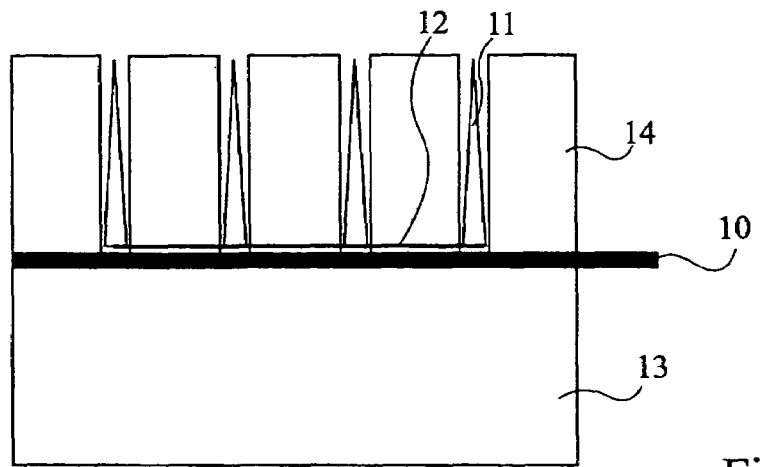
FIGS. 7 to 9 illustrate an example of application of the present invention to a end-to-side anastomosis operation.
Figure 9:
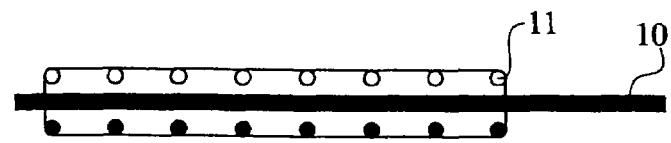

On guide 10 is assembled a "foldable harrow". This harrow is illustrated in unfolded position in FIG. 7A. It is formed of two ranks of needles 11. The needle shapes and dimensions are those currently used to enable sewing of the coronaries. Typically, their base diameter is on the order of a few hundreds of micrometers, and their length is on the order of a few millimeters. At their base, the needles are firmly attached to a single wire 12. This wire defines two sub-assemblies of "right-hand" and "left-hand" needles. The wire first connects the "right-hand" needle assembly, the bases of which are aligned (or form a very elongated half-ellipse), then the "left-hand" needle assembly (see FIG. 9).

Figure 7B:
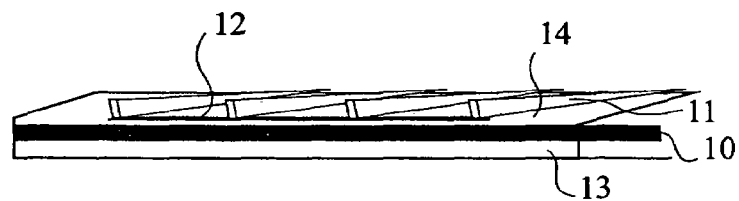

The needles are arranged so that the harrow can take two limiting configurations. In the "catheter" configuration, illustrated in FIG. 7B, the needles are elongated along the catheter axis. In the "sewing" configuration, illustrated in FIG. 7A, the needles are perpendicular to this axis. According to the present invention, the raising of the harrow uses at least one "osmotic motor" comprising a first small balloon 13 arranged on the lower side of the harrow and one or several second small balloons 14 arranged on the upper side of the harrow and arranged to surround the needles. One or the other of osmotic motors 13 and 14 may be replaced with its hydraulic or pneumatic equivalent.

Figure 8:
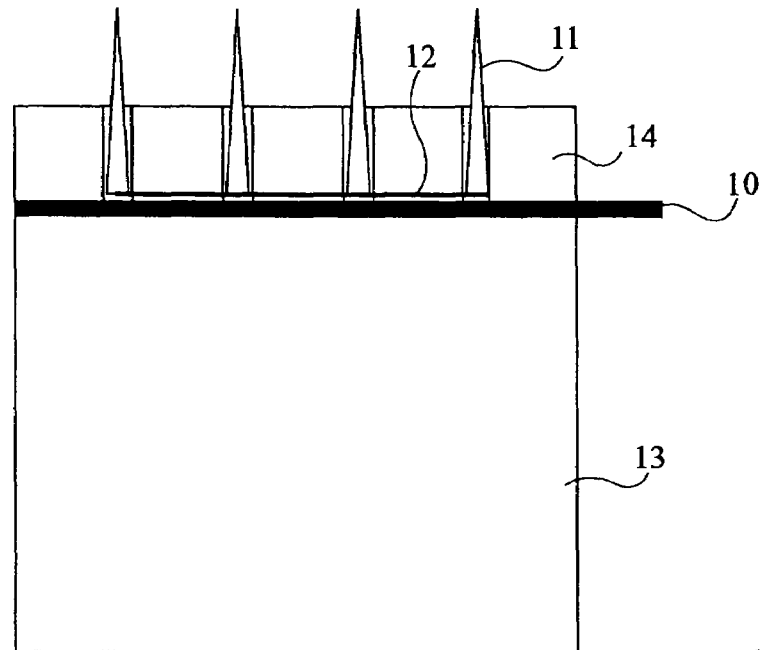

Once the harrow is in place, to enable perforation of the coronary, balloon 13 located under the harrow is "inflated" while "balloons" 14 intended to erect the needles keep their initial pressure. This then leads to the position illustrated in FIG. 8.

When an "osmotic" mechanism is used, these operations are implemented in very natural fashion. The small balloons are indeed deflated when the catheter is introduced. The latter may be protected by a cap, which avoids for these balloons to be in contact with a hydrous medium. The removal of this cap puts the balloons in contact with the blood medium, which activates the osmotic mechanism. If, for example, the osmotically-active bodies have been introduced with a concentration twice smaller in balloons 14 intended to erect the needles than in balloon 13 intended to place these needles flat against the opposite wall, the needles will first erect, then be placed back against the wall, and finally perforate said wall.

3.1.3. Mammary and Coronary Anastomosis

The harrow needles must be used, once they have perforated the coronary wall.

The mammary may have been equipped with a mechanism enabling holding the needles (for example, triple collar, each needle passing before the first collar, behind the second one, and before the third one). The collars are then stretched, which firmly attaches the collars to the needles.

The mammary may have been equipped with a mechanism equivalent to the coronary's. The "coronary" needles must then be immovably attached to the "mammary" needles. Various simple mechanisms can be envisaged (welding, gluing, "twisting" of one needle around the other, etc.).

It may also be devised for the "right-hand" needles to be all raised, to form a series of wire "bridges", under which a cable having its two ends attached to the mammary is introduced.

The motions to be performed are here very simple. When the "right-hand" needles have been firmly attached to the mammary, the same operation is performed for the "left-hand" needles.

3.1.4. Opening of the Communication Between Mammary and Coronary

Up to this stage, the circulation in the coronary has not been interrupted, and the arterial circulation of the mammary is not yet connected to the coronary's. However, the sewing is now ended. The coronary wall still has to be perforated, on its component located between the two rows of needles. The flow pressure will "round up" this opening.

The perforation may be performed mechanically, from an intra-mammary catheter. It may also be electrically devised. The intra-coronary catheter guide is indeed placed flat against the area to be perforated. If it conducts the current, and if it is bare over this area (the rest being isolated), a current can flow through the intra-mammary catheter and the intra-coronary catheter, the assembly behaving as an electric lancet.

The balloons are finally deflated, and the coronary and mammary catheters can then be removed.

3.2. Osmotic Clipping

In vascular surgery, clipping is an advantageous alternative to sewing, since it enables "confronting" two vessels without leaving material in contact with the vascular bed. A mechanical stapler has been described by T. Richard in "AAA: Laparoscopic and/or endovascular repair?", Angio-Techniques 2001. The vessel end is arranged on an "anvil", which enables turning over the free edge, and then having a sufficiently rigid support to enable bearing of the clips.

The disadvantages of this system are:
a relative complexity of the stapler,
the need to use an intermediary vascular substitute (indeed, the stapler must be able to "enter" through the free end of a vessel; the two terminal ends to be anastomosed are thus "equipped", after which an adequate device enables restoring the continuity),
the difficulty of miniaturizing the system.

To overcome these disadvantages, the present invention provides an osmotic clipping device.

First, the free end of each vessel is prepared as follows. An elastic "bag", exhibiting on a portion at least of its surface a semipermeable membrane, is introduced into the vessel. This bag, when inflated, has the shape illustrated in FIGS. 10A and 10B respectively in side view and in top view:
it has a rotational symmetry,
one of its ends 20 is cylindrical,
medium 21 is conical,
the other end comprises digitations 22.

As illustrated in FIGS. 11A to 11C, the bag is introduced while "deflated" into a vessel 24 (FIG. 11A). A ring 25 with as many protrusions 26 as there are intervals between the digitization is installed on vessel 24 (FIG. 11B). Finally, the bag is "inflated".

The different steps of the assembling of two sections of a vessel are illustrated in FIGS. 12A to 12C. The two sections, equipped as that shown in FIG. 11C, are shown opposite to each other as illustrated in FIG. 12A.

Care has been taken over the positioning of protuberances 26 of rings 25 in the spaces left empty by digitizations 22. The protrusions supported by one of the rings are the "male" portions of "press studs", those supported by the other ring being the "female" portions of the same "press studs".

The protuberances are positioned opposite to one another, in complementary fashion, and the rings are then brought close to each other (FIG. 12B) before fastening the "press buttons" (FIG. 12C). Before blocking the last press button element(s), the bags are deflated (for example, by being perforated by means of a needle). In their deflated form, they may be extracted through the orifice remaining between the two vessels.

In the present section 3.2, only the case where the "bags" intended to expand the vessel orifices and to prepare the assembly of the rings provided with protrusions are of osmotic micromuscle type. It should be noted that pneumatically-inflating balloons or shape-memory devices may also be used to perform this operation.

4. Reversible Obturation of a Vessel

A micromuscle according to the present invention may also be used inside of a duct or vessel as a valve that may be opened or closed.

Figure 13A:
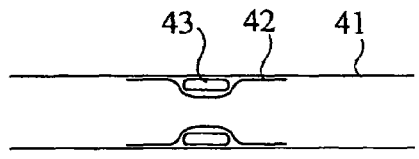
FIGS. 13A and 13B illustrate an example of application of the present invention to a vessel obturation operation.
Figure 13B:
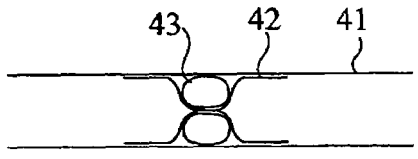

An embodiment of such a valve is illustrated in FIG. 13A in open position and in FIG. 13B in closed position inside of a duct or vessel 41. An endoprosthesis or stent of cylindrical shape 42 formed for example of a shape-memory alloy is surrounded on its median portion with a sleeve 43 formed of a ring-shaped osmotic micromuscle arranged between the cylinder and the vessel. In the case where the vessel walls are resilient, the stent diameter is selected to be slightly greater than that of the vessel to enable anchoring of the stent in the vessel. The expansion capacity of the micromuscle, upon contact with the vessel wall, makes it exert a radial force that compresses both the stent and the wall. The respective forces exerted by the stent and by the micromuscle will be selected to result in the complete obturation of the vessel. One of the previously-described means may be used to stop the compression effect exerted by the micromuscle and "reopen" the vessel.

Such a valve may for example be used for the reversible obturation of the Fallopian tubes. Indeed, the ligature of the Fallopian tubes (natural duct with a diameter of a few millimeters linking the ovaries to the uterus) is used as a contraceptive means. However, this technique results in a quasi-definitive sterilization, possible surgical interventions intended to restore the functionality of these tubes having a high failure ratio.

If a valve of the above-mentioned type is inserted into each of the two tubes, the device operates as a contraceptive means. The introduction of the stent into the tube may be carried out through the vagina or possibly by laparoscopy. When the woman wants to stop this effect, the tube functionality is simply restored.

It can be feared that the internal medium of the Fallopian tubes, though humid, is insufficiently liquid to have a direct action upon an osmotic micromuscle likely to attract a liquid from the surrounding medium. In this case, it will be chosen to use a micromuscle according to the seventh embodiment of the present invention, illustrated in relation with FIGS. 6A and 6B, which has its own liquid reserve. In this application, a reversible micromuscle will preferably be used, that is, a micromuscle in which the second compartment is likely under the effect of a physical or chemical action to "deflate" the first compartment. The contraceptive action is then made reversible.

It should be noted by those skilled in the art that it is also possible to directly use the capacity of acting as a "plug" of the seventh embodiment of the present invention. In this case, the micromuscle is inserted into the Fallopian tube, that it obturates. If later the patient wants to have children again, one of the previously-described micromuscle control modes is applied and enables deflating compartment E1. Nothing then "blocks" the micromuscle any longer in the Fallopian tube, and it naturally falls in the uterine cavity, from which it will be evacuated at the next menstrual period. This specific embodiment has the disadvantage of requiring a new setting into place of the device, if the contraceptive function is subsequently wanted back. It however has the advantage of not leaving a foreign body in the organism, which may pose psychological and physiological problems (the mobility of the tube wall is indeed a significant element of the female fertility, and the permanent presence of a stent could negatively affect it).

Among the many alterations and modifications of the present invention which will occur to those skilled in the art, it should be noted that most of the applications of osmotic micromuscles which have been described may be implemented by using devices having, in these applications, functions similar to those of the osmotic micromuscles, for example, pneumatic or shape-memory devices.

The invention claimed is:

1. A micromuscle device for immersion in a biological medium, the micromuscle device comprising a deformable chamber having at least a portion formed of a semipermeable membrane, the deformable chamber containing a solute capable of being osmotically active, the deformable chamber being designed to have, after inflating by osmotic effect, a predetermined shape, wherein the deformable chamber is surrounded with a sheath or net that determines the predetermined shape, wherein the solute is activable by a product injectable into the biological medium, and wherein the solute is bound to an attachment matrix by a first chemical body from which it can detach in consequence of a competition with another chemical body.

2. The micromuscle device of claim 1, wherein the solute is bound to avidin molecules, the avidin molecules being bound to the attachment matrix by HABA molecules, this bond being breakable by competition with vitamin derivatives, including biotin derivatives, having a greater affinity for the avidin molecules than for the HABA molecules.

3. The micromuscle device of claim 2, wherein the vitamin derivatives include monomer and dimer forms of biotin derivatives.

4. A micromuscle device for immersion in a biological medium, the micromuscle device comprising a deformable chamber having at least a portion formed of a semipermeable membrane, the deformable chamber containing a solute capable of being osmotically active, the deformable chamber being designed to have, after inflating by osmotic effect, a predetermined shape;
    wherein the solute is activable by a product injectable into the biological medium;
    and
    wherein the solute is bound to HABA molecules, the HABA molecules being bound to an attachment matrix by proteins, including at least one of avidin or streptavidin derivatives, this bond being breakable by competition with vitamin derivatives, including biotin derivatives, having a greater affinity for the proteins than for the HABA molecules.

5. A micromuscle device for immersion in a biological medium, the micromuscle device comprising a deformable chamber having at least a portion formed of a semipermeable membrane, the deformable chamber containing a solute capable of being osmotically active, the deformable chamber being designed to have, after inflating by osmotic effect, a predetermined shape, wherein the deformable chamber is formed of two half-cylinders sliding one inside of the other.

6. The micromuscle device of claim 5, wherein opposing ends of the two half-cylinders are connected by a wire.

7. A micromuscle device for immersion in a biological medium, the micromuscle device comprising a deformable chamber having at least a portion formed of a semipermeable membrane, the deformable chamber containing a solute capable of being osmotically active, the deformable chamber being designed to have, after inflating by osmotic effect, a predetermined shape, wherein the semipermeable membrane of the micromuscle device separates the deformable chamber from a second chamber that is in communication with the semipermeable membrane, and wherein the second chamber is formed of a flexible material and contains a reserve of a liquid capable of forming a solution with the solute contained in the deformable chamber.

8. The micromuscle device of claim 7, wherein the solute is capable of being released by physical or chemical action.

* * * * *